United States Patent
Magne-Drisch et al.

(10) Patent No.: US 6,512,154 B1
(45) Date of Patent: Jan. 28, 2003

(54) PRODUCTION OF A XYLENE ISOMER IN THREE STAGES: SEPARATION, ISOMERIZATION WITH A CATALYST WITH AN EUO ZEOLITE BASE AND TRANSALKYLATION WITH RECYCLING OF C10-AROMATIC COMPOUNDS

(75) Inventors: Julia Magne-Drisch, Vilette de Vienne (FR); Gérard Hotier, Chaponost (FR); Jean-François Joly, Lyons (FR); Elisabeth Merlen, Rueil-Malmaison (FR); Fabio Alario, Neuilly sur Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/598,651

(22) Filed: Jun. 22, 2000

(30) Foreign Application Priority Data

Jun. 22, 1999 (FR) .............................. 99 07966

(51) Int. Cl.⁷ .............................. C07C 5/22; C07C 5/12; C07C 15/12
(52) U.S. Cl. ........................ 585/470; 585/475; 585/478; 585/479; 585/477
(58) Field of Search ................................ 585/470, 475, 585/477, 478, 479

(56) References Cited

U.S. PATENT DOCUMENTS

| | | | | |
|---|---|---|---|---|
| 4,341,914 A | | 7/1982 | Berger | 585/474 |
| 4,537,754 A | * | 8/1985 | Casci et al. | 423/277 |
| 4,783,568 A | | 11/1988 | Schmidt | 585/477 |
| 5,284,992 A | * | 2/1994 | Hotier et al. | 585/805 |

FOREIGN PATENT DOCUMENTS

| | | |
|---|---|---|
| EP | 0 051 318 | 5/1982 |
| EP | 0 923 987 | 6/1999 |
| EP | 0 923 987 A1 | 6/1999 |
| FR | 2 768 724 | 3/1999 |

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

A process for the production of at least one xylene isomer, paraxylene, metaxylene or orthoxylene from an aromatic feedstock that has 7 to 10 carbon atoms per molecule. The process comprises a stage for transalkylation of C7- and C9-aromatic compounds, a stage for separation of xylenes and a stage for isomerization of xylenes. The isomerization catalyst used in the process comprises at least one EUO zeolite composition whose crystals are grouped in aggregates that have a grain size with a value of Dv,90 less than or equal to 500 microns and at least one element of group VIII.

22 Claims, 1 Drawing Sheet

PRODUCTION OF A XYLENE ISOMER IN THREE STAGES: SEPARATION, ISOMERIZATION WITH A CATALYST WITH AN EUO ZEOLITE BASE AND TRANSALKYLATION WITH RECYCLING OF C10-AROMATIC COMPOUNDS

TECHNICAL FIELD

This invention relates to a process for conversion of hydrocarbons that makes it possible, starting from fractions that comprise aromatic compounds that have 8 carbon atoms and aromatic compounds that have 7 to 9 carbon atoms per molecule, to produce selectively at least one xylene isomer (aromatic compounds with 8 carbon atoms) that is selected from among metaxylene, paraxylene, and orthoxylene. The process applies in particular to the synthesis of very pure paraxylene to produce an intermediate petrochemical product, terephthalic acid.

PRIOR ART

The production of specific xylene isomer is an important petrochemical process in the synthesis of polyesters, used in particular in the fabric manufacturing industry. It is then important to be able to produce the desired isomer, preferably paraxylene with maximum purity. Several techniques for separating isomers have been developed. Thus, the separation of the isomers can be done by adsorption, for example on a zeolitic sieve, which delivers a fraction that is very high in paraxylene and a fraction that is low in paraxylene and therefore high in ortho- and metaxylene, in the presence of an elution solvent. As the composition of the aromatic feedstocks with 8 carbon atoms varies broadly, however, according to their origin, the para and ortho isomer content relative to the three isomers generally is close to 50%; a single process does not make it possible to maximize the production of the desired isomer. It is then necessary to combine an adsorption stage of the feedstock followed by a stage for isomerization of this fraction that is low in the desired isomer as the one is described in Patent GB 1 420 796. Patent EP 531 191 of the applicant describes a process for the production of paraxylene by treatment in an adsorption zone followed by a crystallization stage of adsorbed paraxylene, whereby the raffinate that is low in paraxylene is sent into a zone for isomerization of xylenes that makes it possible to increase the paraxylene yield.

Actually, during this isomerization stage, the ratio of isomers at equilibrium is reestablished since the desired isomers are produced at the expense of the remaining isomers. The catalyst that is used in the isomerization reactions can be mordenite mixed with other zeolites such as the ZSM-5 zeolite as described in U.S. Pat. Nos. 4,467,129, 4,482,773 and EP 138 617 B. Other catalysts have a mordenite base and were described in, for example, U.S. Pat. Nos. 4,723,051, 4,665,258 and FR 2,477,903.

Catalysts for isomerization of the aromatic fractions with 8 carbon atoms that have a base of EUO-structural-type zeolites, i.e., the EU-1, TPZ-3 and ZSM-50 zeolites, were described by the applicant in Patent Applications FR 97/16, 456 and 97/16,458.

Furthermore, the xylenes can be obtained by the transalkylation reactions of fractions that comprise toluene and aromatic hydrocarbons with 9 carbon atoms, as described in Patent FR 2,761,905 of the applicant, in the presence of a catalyst with a mordenite and binder base that comprises at least one metal that is selected from among the metals of groups VI, VIII and VII. Actually, the transalkylation/dismutation makes it possible to shift methyl groups of aromatic compounds with 9 carbon atoms to compounds such as toluene to obtain xylenes.

Thus, a method of producing paraxylene starting from feedstocks that comprises aromatic compounds that have 7 to 9 carbon atoms is described in U.S. Pat. No. 4,041,091 which discloses a process that combines the stages for separation of xylenes and isomerization starting from a transalkylation effluent to produce paraxylene starting from aromatic feedstocks with 7 and 9 carbon atoms.

Some aromatic fractions, however, that comprise aromatic compounds with 9 carbon atoms and more that are introduced into the transalkylation zone contain a large amount of coke precursor heavy aromatic compounds, which leads to a deactivation of the catalyst. It is known from U.S. Pat. No. 4,341,914 that it is possible to recycle aromatic compounds with 10 carbon atoms from which is removed the majority of these precursors in the transalkylation zone.

Within the scheme of the stages of separation, isomerization and transalkylation, however, constraints in activity and selectivity at the isomerization stage appear, and it is then important to be able to optimize the conditions for isomerization of the isomers of the xylenes, and thereby to reduce the impurities and to increase the paraxylene yield.

SUMMARY

This invention relates to a process for the production of at least one xylene isomer that is selected from among paraxylene, metaxylene and orthoxylene starting from a feedstock that comprises aromatic compounds that have 7 to 10 carbon atoms per molecule that comprises the combination of 3 stages: a stage for transalkylation of aromatic compounds that have 7 carbon atoms (C7) and aromatic compounds that have 9 carbon atoms (C9), a stage for separation of xylenes and a stage for isomerization of xylenes. The feedstock, from which aromatic compounds that have at most 8 carbon atoms and a portion of aromatic compounds that have at least 10 carbon atoms (C10) are removed by treatment in a zone for distillation, is sent into a zone for transalkylation of aromatic compounds that makes it possible to obtain an effluent that comprises aromatic compounds that have 6 to 10 carbon atoms, then after fractionation of the effluent, the benzene-rich fraction can be at least partly recycled at the inlet of the transalkylation zone, the toluene-rich fraction is recycled at the inlet of the transalkylation zone, the fraction that is high in aromatic compounds with 9 carbon atoms and that comprises aromatic compounds with 10 carbon atoms is at least partly recycled at the inlet of the transalkylation zone, and the fraction that is high in aromatic compounds with 8 carbon atoms (C8) is sent into a zone for separation of xylenes to extract the desired isomer, whereby the raffinate that is low in the desired isomer is sent into a zone for catalytic isomerization of the xylenes to produce a mixture that has a xylene composition that is close to the composition at equilibrium, whereby said mixture is recycled at the inlet of the zone for separation of xylenes and/or at the inlet of the zone for distillation of the feedstock. The process according to the invention is characterized in that the catalyst that is used in the catalytic isomerization zone comprises at least one EUO-structural-type zeolite and at least one element of group VIII of the periodic table.

ADVANTAGE

The process according to this invention makes it possible, surprisingly enough, to obtain paraxylene yields that are much higher than those of the prior art thanks to improved performance levels in activity and in selectivity during the isomerization stage, which also leads to a reduction of the recycling volumes as well as a reduction of the necessary amount of isomerization catalyst. Actually, the process according to this invention makes it possible to limit the losses during the isomerization stage, by the use of a catalyst that comprises an EUO-structural-type zeolite. In addition, the process according to the invention makes it possible to treat a larger amount of fresh feedstock for the same amount of catalyst relative to the processes of the prior art. Finally, the process according to the invention that comprises an elimination of the majority of the coke precursor heavy aromatic compounds makes possible a recycling of a fraction that comprises aromatic compounds with 9 and 10 carbon atoms per molecule without loss of yield at transalkylation.

Description

The invention relates to a process for conversion of hydrocarbons and for production of at least one xylene isomer that is selected from among orthoxylene, paraxylene, and metaxylene with an improved desired isomer yield relative to the process of the prior art, by the use in the isomerization zone of a catalyst with an EUO zeolite base and at least one metal of group VIII of the periodic table.

The process according to the invention comprises the following stages:

a) A feedstock that comprises aromatic compounds that have 7 to 10 carbon atoms is introduced into a distillation zone that comprises at least two distillation columns to recover a fraction that comprises in large part C8-aromatic compounds, a fraction that comprises in large part C9-aromatic compounds, a fraction that comprises in large part aromatic compounds that have at least 10 carbon atoms, including a majority of the coke precursor heavy aromatic compounds that are present in the feedstock, b) the fraction that is high in C9-aromatic compounds that is drawn off from distillation zone a), optionally benzene that is introduced by recycling, toluene that is introduced in the form of fresh product and/or by recycling, a recycled fraction that comprises a mixture of C9-aromatic compounds and C10-aromatic compounds, is treated in a catalytic zone for transalkylation of aromatic compounds, c) the effluent of the transalkylation zone is treated in at least one distillation zone to draw off a benzene-rich fraction that can be recycled in the transalkylation zone, a toluene-rich fraction, at least in part recycled in the transalkylation zone, a fraction that comprises C8-aromatic compounds, a fraction that comprises C10-aromatic compounds and in large part C9-aromatic compounds at least in part recycled in the transalkylation zone that is described in b), and a fraction that comprises aromatic compounds that have at least 10 carbon atoms, d) the fraction that is high in C8-aromatic compounds that is drawn off from the distillation zone that is described in c), optionally at least a portion of the effluent of the isomerization zone that is described in e) that is introduced by recycling, the fraction that is high in C8-aromatic compounds that is obtained from the distillation zone that is described in a), are treated in a zone for separation of the xylene isomers so as to recover a first fraction that is high in the desired isomer and a second fraction that is low in the desired isomer, comprising the majority of the other isomers, e) the fraction that is low in the desired isomer that is recovered from the zone for separation of the xylenes that is described in d) is treated in a catalytic zone for isomerization of C8-aromatic compounds, in the presence of a catalyst that comprises at least one EUO-structural-type zeolite and at least one element of group VIII of the periodic table, to produce an effluent that comprises paraxylene, orthoxylene, metaxylene, whereby said effluent is at least in part recycled at the inlet of the separation zone of the xylenes that is described in d), and/or at least in part recycled at the inlet of the distillation zone that is described in a).

During stage a), the feedstock that essentially comprises hydrocarbons that have at least 8 carbon atoms per molecule is fractionated in a distillation zone that comprises at least two columns. The feedstock can be obtained from a gasoline fraction that is obtained from a reforming process, to which optionally in addition are added xylenes that are introduced by recycling of the effluent of the isomerization zone that is described in e).

Distillation zone a) preferably contains two distillation columns, whereby the first column makes it possible to separate the C8-aromatic compounds from the aromatic compounds that have at least 9 carbon atoms, and the second column makes it possible to separate the C9-aromatic compounds from the aromatic compounds that have at least 10 carbon atoms. The fraction that comprises the C8-aromatic compounds is sent into the zone for separation of the xylenes, and the fraction that comprises the C9-aromatic compounds is sent into the transalkylation zone of the aromatic compounds.

Thus, the fraction that comprises the aromatic compounds with 9 carbon atoms is sent into the transalkylation zone of stage b). Toluene is added to the feedstock of the transalkylation zone either by recycling, or by addition of fresh products, or by recycling and addition of fresh products. It is optionally possible to add benzene to the transalkylation feedstock by recycling. The transalkylation zone is characterized in that recycling of a fraction that comprises in large part C9-aromatic compounds and that also comprises C10-aromatic compounds at the inlet of the transalkylation zone is carried out. The transalkylation zone therefore makes it possible to transform the C9-aromatic compounds and the toluene into xylenes with a yield that is enhanced by recycling of the C9/C10-aromatic fraction from which the majority of the coke precursor heavy aromatic compounds are removed. Actually, these precursors are eliminated at least in part in the second distillation column that is included in a), whereby the residual amount is transformed in the transalkylation zone that is described in b), which makes it possible to recycle the C9/C10 fraction and therefore to increase the xylene yield.

Transalkylation stage b) can be implemented in the presence of any catalyst that is known to one skilled in the art. In particular, it is possible to use a catalyst with a base of mordenite and at least one metal that is selected from among the metals of groups VIII, VI and VIIB of the periodic table, such as, for example, nickel, as is described in Patent FR 2,761,905 of the applicant that is incorporated here with reference. The catalyst can also contain at least one element that is selected from groups III and IV of the periodic table, preferably at least one element that is selected from among indium and tin.

In general, the catalyst comprises 40 to 90% by weight of mordenite zeolite that has an Si/Al ratio that is greater than 35, 0.01 to 5% by weight of at least one metal of group VIII, VI and VIIB, optionally 0.01 to 5% by weight of at least one metal of groups III and IV, optionally sulfur, whereby the make-up by weight consists of binder, selected from among, for example, clays, magnesia, aluminas, silicas, titanium oxide, boron oxide, zirconia, aluminum phosphates, titanium phosphates, zirconium phosphates and silica-aluminas. Preferably, the binder is alumina.

The transalkylation zone is implemented at a temperature of between 250 and 600°, preferably between 330 and 500° C., under a pressure that is between 1 and 6 MPa, preferably between 2 and 4.5 MPa, with a feed volumetric flow rate that is expressed in kilogram of feedstock introduced by kilogram of catalyst and per hour, between 0.1 and 10 and preferably between 0.5 and 4; a molar ratio of hydrogen to hydrocarbons of between 2 and 20 and preferably between 3 and 12. The hydrogen that is introduced for the transalkylation can be recycled in the transalkylation zone.

The effluent of the transalkylation zone that comprises the 3 xylene isomers with a composition that is close to the one at equilibrium is then freed of its lightest components that comprise up to 6 carbon atoms, whereby the bottom effluent is then fractionated in stage c) by treatment in at least one distillation zone to recover a fraction that comprises in large part benzene, said fraction can be at least in part recycled to the transalkylation zone, a fraction that comprises in large part toluene, said fraction can be at least in part recycled to the transalkylation zone, a fraction that comprises in large part xylenes that is sent at least in part into the zone for separation of xylenes, a fraction that comprises in large part aromatic compounds with 9 carbon atoms and also comprises aromatic compounds with 10 carbon atoms that is at least in part recycled in the transalkylation zone. The process preferably comprises at least one separate distillation zone per recovered fraction. The process thus preferably comprises a distillation zone for the recovery of light compounds, a distillation zone for the recovery of benzene, a distillation zone for the recovery of toluene, a distillation zone for the recovery of xylenes, a distillation zone for the recovery of the fraction that comprises in large part C9-aromatic compounds and also C10-aromatic compounds.

Stage d) of the process according to the invention comprises the treatment of the fraction that comprises xylenes that is obtained from the transalkylation zone, optionally mixed with the effluent of the isomerization zone that is introduced by recycling, in a zone for separation of the xylenes.

The separation zone comprises at least one adsorption zone in which is adsorbed the majority of the desired isomer or the majority of the undesirable isomers. In an implementation of the invention, the separation zone makes it possible to recover the paraxylene, i.e., the paraxylene is adsorbed and recovered as extract. Other implementations of the invention make it possible to recover the metaxylene based on the adsorbent that is selected. The adsorption zone operates with a simulated moving bed and comprises at least one zeolitic adsorbent bed that operates in the presence of a suitable desorption solvent and under adsorption conditions such that there is obtained, in the case where an effort is made to recover paraxylene, a first fraction that contains solvent, metaxylene, ethylbenzene and orthoxylene, and a second fraction that contains solvent and essentially paraxylene. The paraxylene that is obtained generally has a purity of between 75 and 99.9%. The first fraction is distilled to separate the solvent, on the one hand, and the mixture of metaxylene, orthoxylene and ethylbenzene, on the other hand, and the second fraction is also distilled to recover paraxylene, on the one hand, and the solvent, on the other hand. The first fraction is then sent into the zone for isomerization of xylenes. The solvent can be recycled at the inlet of the separation zone.

The simulated moving bed can be a simulated countercurrent bed or a simulated co-current bed. The elution solvent or desorption solvent is selected from among toluene, paradiethylbenzene. This list is not limiting, and other solvents such as methyl-tert-butyl ether (MTBE) or diisopropyl ether (DIPE) can also be used.

The adsorbents that make it possible to adsorb selectively the paraxylene comprise at least one zeolite that is selected from among the X and Y zeolites whose exchangeable sites are occupied by alkaline or alkaline-earth cations, such as, for example, barium and potassium. The adsorbents that make it possible to adsorb selectively the metaxylene and the orthoxylene are, for example, the Y zeolites that are exchanged with Li, Na, Be, Mg, Ca, Sr, Mn, Cd, Cu and Ni.

In a particular implementation, the zone for separation of the xylenes comprises a crystallization zone that is downstream from the adsorption zone. Thus, for example, the paraxylene that is recovered after distillation of said second fraction is sent into a crystallization zone at a temperature of between +10 and −25° C., and, on the one hand, a mother liquor that is recycled to the adsorption zone is obtained, and, on the other hand, paraxylene crystals that are saturated with mother liquor are obtained, then the paraxylene crystals are washed with a suitable washing solvent to a very high degree of purity, or generally a purity of higher than 99.3% and preferably higher than 99.7%.

As a solvent for washing crystals, it is possible to use, for example, n-pentane, water, purified paraxylene or toluene. The same solvent is preferably used for the desorption and for the washing of crystals, such as, for example, toluene or else purified paraxylene to avoid redistilling the last traces of washing solvent.

The first distilled fraction that is recovered after the stage of separation of the xylenes, comprising orthoxylene, metaxylene and ethylbenzene, is treated in an isomerization zone. Isomerization stage e) is implemented in the presence of a catalyst that comprises an EUO-structural-type zeolite, for example the EU-1 zeolite.

The catalyst that is used in the isomerization stage thus comprises at least one EUO zeolite, i.e., the EU-1, TPZ-3 and ZSM-50 zeolites.

The EUO-structural-type EU-1 zeolite, already described in the prior art, has a monodimensional microporous network, whose pore diameter is 4.1×5.7 Å (1 Å=1 angstrom=$1.10^{-10}$m) ("Atlas of Zeolites Structure Types," W. M. Meier and D. H. Olson, 4th Edition, 1996). In contrast, N. A. Briscoe et al. taught in an article of the journal Zeolites (1988, 8, 74) that these monodimensional channels have side pockets with a depth of 8.1 Å and diameter 6.8×b 5.8 Å. The synthesis method of the EU-1 zeolite and its physico-chemical characteristics were described in Patent EP-B 1-42 226.

U.S. Pat. No. 4,640,829 relates to the ZSM-50 zeolite, which according to the "Atlas of Zeolites Structure Types," W. M. Meier and D. H. Olson, 4th Edition, 1996, is of the EUO-structural type. Patent EP-A1-51 318 relates to the TPZ-3 zeolite, which is of the EUO-structural type according to the "Atlas of Zeolites Structure Types," W. M. Meier and D. H. Olson, 4th Edition, 1996.

The EUO-structural-type zeolite is at least in part in acid form and comprises silicon and at least one element T that is selected from the group that is formed by aluminum, iron, gallium and boron, preferably aluminum, with an overall Si/T atomic ratio that is higher than 5.

The catalyst also comprises at least one matrix that comprises at least one compound that is selected from the group that is formed by clays, magnesia, aluminas, silicas, titanium oxide, boron oxide, zirconia, aluminum phosphates, titanium phosphates, zirconium phosphates and silica-aluminas. The matrix is preferably alumina. The catalyst comprises at least one element of group VIII of the periodic table, preferably selected from among platinum and palladium, and can also contain optionally at least one metal that is selected from among the metals of groups IIIA and IVA, preferably selected from among tin and indium and optionally sulfur.

The isomerization catalyst comprises by weight relative to the total catalyst mass:

1 to 90% by weight of at least one EUO-structural-type zeolite, preferably 3 to 60%, and even more preferably 4 to 40%, 0.01 to 2% by weight of at least one metal of group VIII, preferably 0.05 to 1%, optionally 0.01 to 2% of at least one additional element that is selected from groups IIIA and IVA of the periodic table, preferably 0.05 to 1%, optionally sulfur, a binder that ensures the make-up by weight to 100% of the catalyst.

According to a preferred embodiment of the invention, a catalyst will be used that comprises an EUO-structural-type zeolite whose crystal size is less than 5 micrometers ($\mu$m), preferably less than 0.5 $\mu$m and even more preferably less than 0.2 $\mu$m. These crystals or crystallites are often grouped into aggregates that have a grain size such that the value of Dv,90 is less than or equal to 500 $\mu$m, often less than 400 $\mu$m and most often less than 200 $\mu$m, and preferably less than 50 $\mu$m. The size of the aggregates is determined by grain size with laser diffraction. After a measurement, the suspension is subject to ultrasound for thirty seconds, then a new measurement is taken. The ultrasound that is used is characterized by a power of 50 W and a frequency of 50 kHz. This procedure is repeated until the result no longer varies (at $\mp$5%). The volume-defined size distribution of the aggregates is calculated starting from the light signals that are collected by the detectors and with Fraunhofer's theory. Dv,X is defined as being the diameter of the equivalent sphere such that X% by volume of the aggregates has a size that is smaller than said diameter. These characteristics will be obtained directly during the synthesis of the zeolite and/or by any method that makes it possible to reduce the size of the aggregates, such as, for example, post-synthesis grinding or else a suitable kneading before shaping.

The catalyst is preferably prepared as described in the incorporated here as reference. Thus, the catalyst preferably has a dispersion of the metal of group VIII of between 50 and 100%, and more preferably between 60 and 100% and even more preferably between 70 and 100%, a macroscopic distribution coefficient of said metal of group VIII between 0.7 and 1.3, preferably between 0.8 and 1.2. Preferably, the catalyst is shaped in ball or extrudate form and has a mechanical resistance such that the bed crushing value is greater than 0.7 MPa.

The isomerization zone is operated at a temperature of about 300° C. to 500° C., preferably about 320° C. to 450° C., and even more preferably about 350° C. to 420° C., at a partial hydrogen pressure of about 0.3 to 1.5 MPa, preferably about 0.4 to 1.2 MPa, at a total pressure of about 0.45 to 1.9 MPa, preferably about 0.6 to 1.5 MPa, at a PPH (feedstock weight/catalyst weight/hour) of about 0.25 h−1 to 30 h−1, preferably about 1 to 10 h−1, and very often 2 h−1 to 7 h−1. The hydrogen that is introduced to carry out the isomerization can be recycled in said isomerization zone.

In a particular implementation of the isomerization stage, the isomerization zone comprises a recycling as described in the patent application of the applicant FR 98/04,526, incorporated here by reference. The process then comprises at least one distillation zone downstream from the isomerization zone to recover a fraction that contains in large part aromatic compounds that contain at least 8 carbon atoms per molecule and that is sent into the zone for separation of xylenes of stage d) and to recover a fraction that comprises compounds with a boiling point of about 80° C. to 135° C. and more particularly at least one of the compounds that are selected from the group that consists of naphthenes with 8 carbon atoms per molecule, paraffins with 8 carbon atoms per molecule, benzene and toluene, at least one of the compounds of said fraction, isolated from the whole of the fraction by treatment in at least one distillation zone, that can be recycled at the inlet of the isomerization zone. The percentage by mass of recycled compounds relative to the total feedback that is part of the isomerization zone is between 0.01 and 20%. Actually, surprisingly enough, the fact of recycling at least one compound with a boiling point between 80° C. and 135° makes it possible to reduce the parasitic reactions of isomerization and also makes it possible to reduce the volume of the feedstock of the transalkylation zone, which, combined with the performance levels of the catalyst, allows considerable savings for the device. Preferably, the naphthenes with 8 carbon atoms are recycled in the iosmerization zone, whereby the other compounds of the fraction with a boiling point between 80° C. and 135° C., such as toluene and paraffins, can be recovered at this level of the process.

The output effluent of the isomerization zone that comprises the three xylene isomers in a ratio that is essentially close to that of the thermodynamic equilibrium is then freed of its lightest components that have up to 6 carbon atoms, whereby the residual fraction is either at least in part recycled in the zone for separation of xylenes, mixed with the aromatic C8-fraction that is drawn off from the distillation zone of the feedstock of stage a), and mixed with the C8-aromatic fraction that is recovered in stage c) at the outlet of the transalkylation zone, or at least in part recycled in the zone for separation of xylenes and in part recycled in the zone for distillation of the feedstock.

Figure 1:
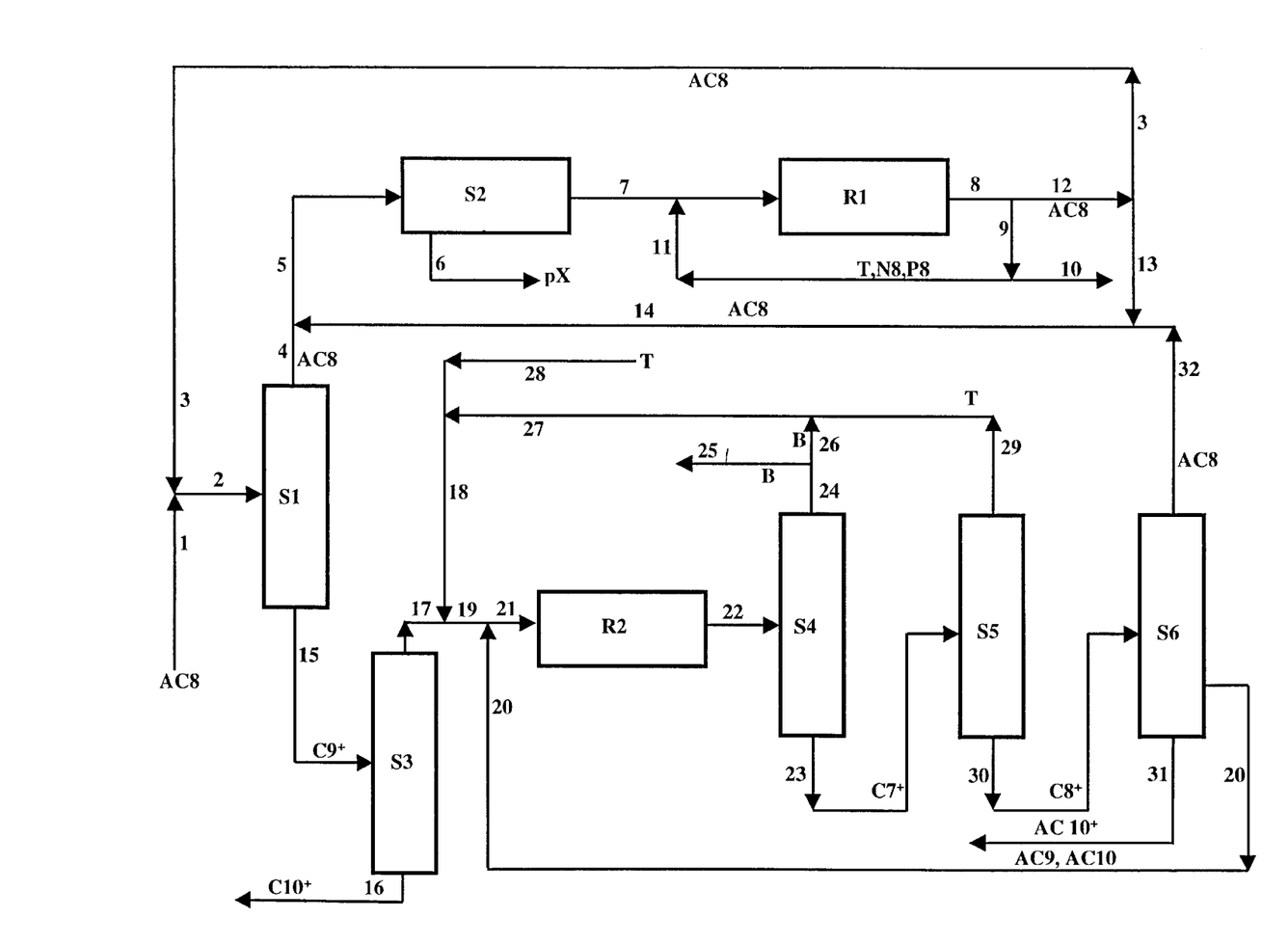
FIG. 1 illustrates one of the embodiments of the process.

The feedstock that comprises aromatic compounds that have 7 to 10 carbon atoms (1) is introduced, optionally in a mixture (2) with the C8-aromatic compounds that are obtained from the output effluent of isomerization zone (3), into a distillation zone S1. The column bottom that comprises the aromatic compounds that have at least 9 carbon atoms is sent via line (15) into a second distillation zone S3 from which the aromatic compounds that have at least 10 carbon atoms (16) are eliminated in part, and at the top of the column, a fraction that comprises a majority of C9-aromatic compounds and also C10-aromatic compounds (17) are recovered. Fraction (17) is sent, mixed (19) with toluene that is introduced in the form of fresh product and/or recycling (27, 28, 18) and mixed with a recycled effluent that comprises C9- and C10-aromatic compounds (20) in a catalytic transalkylation zone R2 via line (21). Output effluent (22) is then treated in a column S4 from which at the top, a benzene-rich fraction (24) is recovered, either eliminated (25) or recycled in transalkylation zone (26, 27, 18); whereby bottom effluent (23) is sent into a column from which a toluene-rich fraction (29) is recovered, recycled (29, 27, 18) in the transalkylation zone, whereby bottom effluent (30) is sent into a zone for separation S6 from which at the top, there are recovered a fraction that is high in C8-aromatic compounds (32), a fraction (20) that comprises C9- and C10-aromatic compounds recycled at the inlet of the transalkylation zone, and a fraction that comprises aromatic compounds that have at least 10 carbon atoms, eliminated via line (31). The fraction that is high in C8-aromatic compounds (32) is sent into mixture (14) with output isomerization effluent (13) that comprises C8-aromatic compounds in the zone for separation of xylenes S2 and in a mixture (5) with top fraction (4) of distillation zone S1 that comprises the C8-aromatic compounds. The extract from separation zone S2 is recovered via line (6), and raffinate (7) is sent into a catalytic zone for isomerization of xylenes R1, from which is recovered an effluent (8) that is fractionated in a fraction (9) that comprises at least one compound with a boiling point of between 80 and 135° C., recycled at the inlet of isomerization zone (11), whereby the light compounds are eliminated via line (10) and a fraction (12) that comprises the C8-aromatic compounds, recycled either at the inlet of the separation zone of xylenes S2 via line (13) or at the inlet of distillation zone S1 via line 3.

EXAMPLES

Example According to the Invention

The following example illustrates the invention. It is carried out according to FIG. 1 with:
- recycling of the naphthenic fraction to the inlet of the isomerization reactor,
- recycling of the output effluent of the isomerization zone to the inlet of column S1,
- recycling to the transalkylation inlet of a portion of the benzene that is collected following separation S4 at the transalkylation outlet.

The feedstock (line 2) that enters into separation column S1 has the following composition (% by weight):

| | |
|---|---|
| Toluene | 0.08 |
| Paraffins with 8 carbon atoms | 0.37 |
| Naphthenes with 8 carbon atoms | 0.02 |
| Ethylbenzene | 7.79 |
| p-Xylene | 19.18 |
| m-Xylene | 42.19 |
| o-Xylene | 18.85 |
| AC9 | 9.25 |
| AC10+ | 2.26 |

This feedstock corresponds to the mixture of 22.0% by weight of a fresh feedstock (line 1) that comprises 40% by weight of AC9 and 10% by weight of AC10+, and 78.0% by weight of the AC8 mixture obtained from the isomerate and recycled (line 3).

After separation (S1), the column bottom is sent (line 15) to a second distillation (S3). This feedstock comprises a mixture of AC9/AC10+ (80.3/19.7) by weight. This distillation column S3 made it possible to eliminate (line 16) 52.1% by weight of the AC 10+ that is introduced. At the top of the column (line 17), the feedstock that is sent to the transalkylation zone consists of 89.7% by weight of AC9 and 10.3% by weight of AC 10.

The AC9, a portion of the AC 10, toluene and benzene that are obtained from the transalkylation zone, are recycled at the inlet of the reactor and mixed with the top of the column (line 17) and with an addition of toluene so as to provide toluene/AC9 ratios (50/50) by weight. The feedstock at the inlet of transalkylation reactor (R2) (line 21) therefore has the following composition (% by weight):

| | |
|---|---|
| Benzene | 6.43 |
| Toluene | 44.46 |
| AC9 | 44.46 |
| AC10+ | 4.65 |

This feedstock is treated in transalkylation reactor (R2) under the following conditions:

| | |
|---|---|
| Catalyst | Ni/mordenite/alumina (0.69%/79.5%/19.8%) |
| Temperature | 430° C. |
| H$_2$/hydrocarbon ratio | 5:1 |
| Pressure | 30 bar |

The effluent (line 22) that is obtained from the transalkylation zone has the following composition (% by weight):

| | |
|---|---|
| C6– | 0.86 |
| Benzene | 12.63 |
| Toluene | 30.09 |
| Ethylbenzene | 2.28 |
| p-Xylene | 6.28 |
| m-Xylene | 13.40 |
| o-Xylene | 5.98 |
| AC9 | 22.86 |
| AC10+ | 5.42 |

The AC9 conversion is 48.5% by weight, the toluene conversion is 32.2% by weight, and the xylene selectivity is 71.66%.

The benzene is separated (column S4) and recycled at 50% by weight at the inlet of the transalkylation reactor (line 26). The toluene is then separated (column S5) and recycled at the inlet of the reactor (line 29).

The C8-aromatic compounds, separated with column S6, are recycled at the inlet of separation zone S2.

The C8-aromatic compound yield, relative to the feedstock that is treated in the transalkylation zone, is 28% per pass, and the recycled composition of the C8-aromatic compounds is as follows (% by weight):

| | |
|---|---|
| Ethylbenzene | 8.15 |
| p-Xylene | 22.47 |
| m-Xylene | 47.96 |
| o-Xylene | 21.42 |

Column S6 makes it possible to eliminate (line 31) 60% by weight of the AC 10+, and the remainder of the AC9 and AC10 is recycled at the inlet of the transalkylation zone.

At the inlet of separation zone S2, the treated feedstock (line 5) corresponds to the mixture of the AC8 that is obtained from the transalkylation zone and at the top of column S1. The feedstock has the following composition (% by weight):

| | |
|---|---|
| Toluene | 0.08 |
| Paraffins with 8 carbon atoms | 0.37 |

-continued

| | |
|---|---|
| Naphthenes with 8 carbon atoms | 0.02 |
| Ethylbenzene | 8.73 |
| p-Xylene | 21.77 |
| m-Xylene | 47.72 |
| o-Xylene | 21.32 |

The separation of the paraxylene (S2) takes place under the following conditions:

Adsorption in a countercurrent simulated moving bed implementation without crystallization):

| | |
|---|---|
| Sieve | Ba-X, 5.5% $H_2O$ measured by the loss due to ignition (LOI) at 950° C. |
| Temperature | 170° C. |
| Number of beds | 24 |
| Minimum pressure | 9 bar |
| PDEB/feedstock ratio | 1.5:1 |
| Productivity | 70.8 kg of pX/$m^3$ of sieve/hour |

The paraxylene that is recovered as extract (line 6) has a purity of 99.8% and a yield of 96% or 20.9% by weight of paraxylene that is collected relative to the feedstock that is treated in the separation zone.

The raffinate (line 7), after distillation of the desorption solvent (separation not shown in the figure), has the following composition (% by weight):

| | |
|---|---|
| Toluene | 0.10 |
| Paraffins with 8 carbon atoms | 0.47 |
| Naphthenes with 8 carbon atoms | 0.03 |
| Ethylbenzene | 11.03 |
| p-Xylene | 1.10 |
| m-Xylene | 60.32 |
| o-Xylene | 26.95 |

This raffinate (line 7), mixed with the naphthenes with 8 carbon atoms as well as the paraffins with 8 carbon atoms and toluene that are obtained from the isomerization reactor and recycled (line 11), is isomerized in isomerization zone (R1) under the following conditions:

| | |
|---|---|
| Catalyst | Pt/EU-1 zeolite with a ratio of Si/Al = 18/binder (alumina) (0.3%/10%/89.7%) |
| Temperature | 380° C. |
| $H_2$/hydrocarbon ratio | 4:1 |
| Pressure | 8 bar |
| The isomerization effluent (line 8) has the following composition (% by weight) | |
| C6– | 0.81 |
| Benzene | 0.08 |
| Toluene | 0.56 |
| Paraffins with 8 carbon atoms | 0.61 |
| Naphthenes with 8 carbon atoms | 8.63 |
| Ethylbenzene | 6.15 |
| p-Xylene | 19.70 |
| m-Xylene | 43.55 |
| o-Xylene | 19.33 |
| AC9 | 0.51 |
| AC10+ | 0.07 |

The isomerization catalyst with an EU-1 zeolite base therefore made it possible to convert 39% by weight of ethylbenzene, and the yield of the isomerization zone, in aromatic compounds with 8 carbon atoms+naphthenes with 8 carbon atoms, is 98%.

This isomerate is sent into a separation zone (not shown in the figure) that makes it possible to eliminate the (C6-) light compounds (line 10) and to separate the fraction that contains toluene as well as the naphthenes and paraffins with 8 carbon atoms (line 11). This fraction is recycled at the inlet of the isomerization reactor, which makes it possible to eliminate the losses of aromatic compounds with 8 carbon atoms in the form of naphthenes by hydrogenation reactions, whereby these reactions are balanced under the applied operating conditions. The volume of recycling to the isomerization corresponds to 9.8% by weight of the feedstock that enters the isomerization reactor, and the net losses (non-recyclable compounds) are 0.89% by weight.

The AC8+ mixture that is collected after separation (line 12) has the following composition (% by weight):

| | |
|---|---|
| Ethylbenzene | 6.89 |
| p-Xylene | 22.06 |
| m-Xylene | 48.76 |
| o-Xylene | 21.64 |
| AC9 | 0.57 |
| AC10+ | 0.08 |

Example for Comparison (Not In Accordance with the Invention)

The following example is produced according to FIG. 1 with:

recycling of the naphthenic fraction to the inlet of the isomerization reactor, recycling of the isomerate to the inlet of the S1 column, recycling to the transalkylation inlet of benzene that is collected by separation S4 at the transalkylation outlet as in the case of the preceding example that illustrates the invention.

To compare the paraxylene yield performance levels that are obtained, the recycling volumes and the amounts of catalyst of the entire process scheme, the same fresh feedstock as the one that is described in the preceding example that illustrates the invention is treated.

The feedstock (line 2) that enters separation column S1 has the following composition (% by weight):

| | |
|---|---|
| Toluene | 0.07 |
| Paraffins with 8 carbon atoms | 0.34 |
| Naphthenes with 8 carbon atoms | 0.02 |
| Ethylbenzene | 8.96 |
| p-Xylene | 17.16 |
| m-Xylene | 42.77 |
| o-Xylene | 19.48 |
| AC9 | 8.94 |
| AC10+ | 2.25 |

This feedstock corresponds to the mixture of 20.1% by weight of fresh feedstock (line 1), and 79.9% by weight of the AC8 mixture obtained from the isomerate and recycled (line 3).

After separation (S1), the column bottom is sent (line 15) to a second distillation (S3). This feedstock comprises an AC9/AC10+ mixture (79.9/20.1) by weight. This distillation column S3 made it possible to eliminate (line 16) 51.3% by weight of the AC10+that is introduced. At the top of the column (line 17), the feedstock that is sent to the transalkylation zone consists of 89.5% by weight of AC9 and 10.5% by weight of AC10.

The AC9, a portion of AC10, toluene and benzene that are obtained from the transalkylation zone are recycled at the inlet of the reactor and mixed with the top of the column (line 17) and with an addition of toluene so as to provide toluene/AC9 ratios (50/50) by weight. The feedstock at the inlet of the transalkylation reactor (R2) (line 21) therefore has the following composition (% by weight):

| | |
|---|---|
| Benzene | 6.63 |
| Toluene | 44.32 |
| AC9 | 44.32 |
| AC10+ | 4.73 |

This feedstock is treated in transalkylation reactor (R2) under the same conditions as the preceding example. The performance levels that are obtained are equivalent (toluene conversion and AC9 conversion and xylene selectivity).

The AC8 yield, relative to the feedstock that is treated in the transalkylation zone, is 27.9% per pass.

At the inlet of separation zone S2, the treated feedstock (line 5) corresponds to the mixture of AC8 obtained from the transalkylation zone and at the top of column S1. The feedstock has the following composition (% by weight):

| | |
|---|---|
| Toluene | 0.07 |
| Paraffins with 8 carbon atoms | 0.34 |
| Naphthenes with 8 carbon atoms | 0.02 |
| Ethylbenzene | 9.87 |
| p-Xylene | 19.68 |
| m-Xylene | 48.14 |
| o-Xylene | 21.87 |

The separation of paraxylene (S2) took place under the following conditions:

Adsorption in a countercurrent simulated moving bed (stand-alone version):

| | |
|---|---|
| Sieve | Ba-X, 5.5% $H_2O$ measured by the loss due to ignition (LOI) at 950° C. |
| Temperature | 170° C. |
| Number of beds | 24 |
| Minimum pressure | 9 bar |
| PDEB/feedstock ratio | 1.5:1 |
| Productivity | 64.5 kg of pX/m³ of sieve/hour |

The paraxylene that is recovered as extract (line 6) has a purity of 99.8% and a yield of 91.8% or 18.1% by weight of paraxylene that is collected relative to the feedstock that is treated in the separation zone. The paraxylene yield is less (91.8% versus 96%) relative to the preceding example according to the invention because the treated feedstock contains more ethylbenzene and less paraxylene. The productivity drops from 70.8 to 64.5 kg of pX/m³ of sieve/hour.

The raffinate (line 7) after distillation of the desorption solvent (separation not shown in the figure) has the following composition (% by weight):

| | |
|---|---|
| Toluene | 0.09 |
| Paraffins with 8 carbon atoms | 0.41 |
| Naphthenes with 8 carbon atoms | 0.02 |
| Ethylbenzene | 12.05 |
| p-Xylene | 1.97 |

-continued

| | |
|---|---|
| m-Xylene | 58.76 |
| o-Xylene | 26.70 |

This raffinate (line 7), mixed with the naphthenes with 8 carbon atoms as well as the paraffins with 8 carbon atoms and toluene that are obtained from the isomerization reactor and recycled (line 11), is isomerized in isomerization zone (R1) under the same operating conditions as in the preceding example but with a catalyst with a mordenite base:

Catalyst: Pt/mordenite/binder (alumina) (0.29%/15%/84.7%)

To carry out the isomerization under the same operating conditions, the catalytic volume has to be increased by 4.0% by weight relative to the amount that is used in the preceding example according to the invention, because the amount of raffinate is larger, the smaller the paraxylene yield.

The isomerization effluent (line 8) has the following composition (% by weight):

| | |
|---|---|
| C6- | 0.98 |
| Benzene | 0.29 |
| Toluene | 1.20 |
| Paraffins with 8 carbon atoms | 0.81 |
| Naphthenes with 8 carbon atoms | 8.86 |
| Ethylbenzene | 7.43 |
| p-Xylene | 16.88 |
| m-Xylene | 42.84 |
| o-Xylene | 19.43 |
| AC9 | 1.01 |
| AC10+ | 0.27 |

The isomerization catalyst with a mordenite base therefore made it possible to convert 31.8% by weight of ethylbenzene, and the yield of the isomerization zone, in aromatic compounds with 8 carbon atoms+naphthenes with 8 carbon atoms, is 96.2%.

This isomerate is sent into a separation zone (not shown in the figure) that makes it possible to eliminate the (C6-) light compounds (line 10) and to separate the fraction that contains toluene as well as naphthenes and paraffins with 8 carbon atoms (line 11). This fraction is recycled at the inlet of the isomerization reactor, which makes it possible to eliminate the losses of aromatic compounds with 8 carbon atoms in the form of naphthenes by hydrogenation reactions, whereby these reactions are balanced under the applied operating conditions. The volume of recycling to the isomerization corresponds to 10.9% by weight of the feedstock that enters the isomerization reactor, and the net losses (non-recyclable compounds) are 1.27% by weight.

The AC8+ mixture that is collected after separation (line 12) has the following composition (% by weight):

| | |
|---|---|
| Ethylbenzene | 8.46 |
| p-Xylene | 19.21 |
| m-Xylene | 48.76 |
| o-Xylene | 22.11 |
| AC9 | 1.15 |
| AC10+ | 0.31 |

In the example concerned, it was therefore noted that the use of an isomerization catalyst of the AC8 with an EU-1-type zeolite base in the process scheme described made it possible:

to increase considerably the amount of paraxylene that is extracted at separation S2 (feedstock that is more concentrated in paraxylene and improved extraction yield), to reduce the catalytic volume of isomerization, to reduce the volume of recycling of the naphthenic fraction on isomerization, and, for the same composition of treated fresh feedstock and volumes (catalyst and columns) that are identical in the transalkylation zone, the amount of treated fresh feedstock per pass is larger (22.0% by weight versus 20. 1% by weight with mordenite).

What is claimed is:

1. A process for the production of at least one xylene isomer that is paraxylene, orthoxylene, or metaxylene comprising the following stages:
    a) A feedstock that comprises aromatic compounds having 7 to 10 carbon atoms, optionally mixed with the output effluent of the isomerization zone that is described in e), is introduced into a distillation zone that comprises at least two columns to recover a fraction that comprises in large part C8-aromatic compounds, a fraction that comprises in large part C9-aromatic compounds, a fraction that comprises in large part aromatic compounds that have at least 10 carbon atoms, including a majority of the coke precursor heavy aromatic compounds that are present in the feedstock,
    b) the fraction that is high in C9-aromatic compounds that is drawn off from the distillation zone in a), toluene that is introduced in the form of fresh product and/or by recycling, a recycled fraction that comprises a mixture of C9-aromatic compounds and C10-aromatic compounds, are treated in a catalytic transalkylation zone,
    c) the effluent of the transalkylation zone that is described in b) is treated in at least one distillation zone to draw off a benzene-rich fraction, a toluene-rich fraction that is at least in part recycled in the transalkylation zone that is described in b), a fraction that comprises C8-aromatic compounds, a fraction that comprises C10-aromatic compounds and in large part C9-aromatic compounds at least in part recycled in the transalkylation zone that is described in b), and a fraction that comprises aromatic compounds that have at least 10 carbon atoms,
    d) the fraction that is high in C8-aromatic compounds that is drawn off from the distillation zone that is described in c), optionally at least a portion of the effluent of the isomerization zone that is described in e), the fraction that is high in C8-aromatic compounds that is obtained from the distillation zone that is described in a), are treated in a zone for separation of the xylene isomers so as to recover a first fraction that is high in the desired isomer and a second fraction that is low in the desired isomer, comprising the majority of the other isomers,
    e) the fraction that is low in the desired isomer that is recovered from the separation zone that is described in d) is treated in a catalytic zone for isomerization of xylenes, in the presence of a catalyst that comprises at least one EUO zeolite composition whose crystals are grouped in aggregates that have a grain size with a value of Dv,90 less than 400 microns and at least one element of group VIII of the periodic table, to produce an effluent that comprises paraxylene, orthoxylene, metaxylene, whereby said effluent is at least in part recycled at the inlet of the separation zone of the xylenes that is described in d), and/or at least in part recycled at the inlet of the distillation zone that is described in a).

2. A process according to claim 1, such that the desired xylene isomer is paraxylene.

3. A process according to claim 1 such that the desired xylene isomer is metaxylene.

4. A process according to claim 1, such that at least a portion of the benzene that is drawn off from the distillation zone that is described in stage c) is recycled at the inlet of the transalkylation zone that is described in b).

5. A process according claim 1, such that the distillation zone that is described in a) comprises a first distillation zone to separate at least in part the C8-aromatic compounds from the aromatic compounds that have at least 9 carbon atoms and a second distillation zone that makes it possible to separate at least in part the C9-aromatic compounds and the compounds that have at least 10 carbon atoms.

6. A process according to claim 1, such that the catalyst that is used in the isomerization zone that is described in e) has a base of at least one EUO zeolite composition that is EU-1, TPZ-3, or ZSM-50 zeolites, comprising silicon and at least one element T that is aluminum, iron, gallium or boron, with an overall Si/T ratio that is greater than 5.

7. A process according to claim 1, such that the catalyst of the isomerization zone that is described in e) has a base of at least one EUO zeolite composition whose crystal size is less than 5 microns.

8. A process according to claim 1, such that the catalyst that is used in the isomerization zone that is described in e) also comprises at least one element that is a metal of groups IIIA or IVA.

9. A process according to claim 1, such that the catalyst that is used in the isomerization zone that is described in e) has a dispersion of the metal of group VIII of between 50% and 100%.

10. A process according to claim 1, such that the catalyst that is used in the isomerization zone that is described in e) has a macroscopic distribution coefficient of the metal of group VIII of between 0.7 and 1.3.

11. A process according to claim 1, such that the isomerization zone that is described in b) is operated at a temperature of between 300 and 500° C., at a partial hydrogen pressure of between 0.3 and 1.5 MPa, at a total pressure of between 0.45 and 1.9 MPa and with a PPH of between 0.25 $h^{-1}$ and 30 $h^{-1}$.

12. A process according to claim 1, such that at least one fraction of the output isomerization effluent is recycled in the isomerization zone that is described in e), whereby said fraction comprises at least one compound with a boiling point of between 80 and 135° C.

13. A process according to claim 1, such that the catalyst that is used in the transalkylation zone that is described in b) has a mordenite base and comprises at least one metal of group VIB, VII and VIII of the periodic table.

14. A process according to claim 1, such that the catalyst is used in the transalkylation stage that is described in b) also comprises at least one element from groups IVA or III of the periodic table.

15. A process according to claim 1, such that the transalkylation stage that is described in b) is operated at a temperature of between 250° C. and 600° C. under a pressure of between 1 and 6 MPa, with a PPH of between 0.1 h–1 and 10 h–1, with a hydrogen to hydrocarbon molar ratio of between 2 and 20.

16. A process according to claim 1, such that the zone for separation of the xylenes that is described in d) is a simulated moving bed adsorption zone in the presence of a zeolitic sieve.

17. A process according to claim 16, such that the zeolitic sieve that is used in stage d) to extract specifically the paraxylene comprises at least one X, or Y zeolite whose exchangeable sites are occupied by at least one alkaline or alkaline-earth cation.

18. A process according to claim 16, such that the zeolitic sieve that is used in stage d) to extract specifically the metaxylene and the orthoxylene comprises a Y zeolite that is exchanged with at least one of Li, Na, Be, Mg, Ca, Sr, Mn, Cd, Cu or Ni.

19. A process according to claim 1, such that the adsorption stage of stage d) takes place in the presence of an elution solvent that is toluene, paradiethylbenzene, methyl-tert-butyl ether MTBE, or diisopropyl ether (DIPE).

20. A process according to claim 1, such that the separation zone of stage d) comprises a crystallization zone downstream from the adsorption.

21. A process according to claim 1, wherein the catalyst that comprises at least one EUO zeolite composition whose crystals are grouped in aggregates have a grain size with a value of Dv,90 less than 200 microns.

22. A process according to claim 1, wherein the catalyst that comprises at least one EUO zeolite composition whose crystals are grouped in aggregates have a grain size with a value of Dv,90 less than 50 microns.

* * * * *